US008216266B2

(12) United States Patent
Hively (10) Patent No.: US 8,216,266 B2
(45) Date of Patent: Jul. 10, 2012

(54) GASTRIC BARIATRIC APPARATUS WITH SELECTIVE INFLATION AND SAFETY FEATURES

(76) Inventor: Robert L. Hively, Dunbar, WV (US)

(*) Notice: Subject to any disclaimer, the term of this patent is extended or adjusted under 35 U.S.C. 154(b) by 1179 days.

(21) Appl. No.: 11/155,400

(22) Filed: Jun. 16, 2005

(65) Prior Publication Data

US 2007/0083224 A1  Apr. 12, 2007

(51) Int. Cl.
*A61M 29/00* (2006.01)
*A61B 17/08* (2006.01)

(52) U.S. Cl. .......... 606/192; 606/191; 606/153
(58) Field of Classification Search .......... 606/191–195, 606/153; 604/909, 99.01–99.04, 103–103.14, 604/96.01; 623/23.64–23.65, 23.67–23.68; 128/898
See application file for complete search history.

(56) References Cited

U.S. PATENT DOCUMENTS

| 1,499,962 | A |   | 7/1924  | Barnes |
| 2,643,581 | A |   | 6/1953  | Wehrenfennig |
| 3,185,503 | A |   | 5/1965  | Angle |
| 3,570,494 | A | * | 3/1971  | Gottschalk .............. 606/196 |
| 3,596,936 | A |   | 8/1971  | Dieckmann et al. |
| 4,607,618 | A |   | 8/1986  | Angelchik |
| 4,648,683 | A |   | 3/1987  | Botka |
| 4,694,827 | A | * | 9/1987  | Weiner et al. ............ 606/192 |
| 4,739,758 | A |   | 4/1988  | Lai et al. |
| 4,878,695 | A |   | 11/1989 | Whitham |
| 4,899,747 | A |   | 2/1990  | Garren et al. |
| 4,925,446 | A |   | 5/1990  | Garray et al. |
| 4,944,749 | A | * | 7/1990  | Becker .............................. 623/8 |
| 5,002,772 | A | * | 3/1991  | Curatolo et al. ............ 424/438 |
| 5,084,061 | A |   | 1/1992  | Gau et al. |
| 5,188,399 | A |   | 2/1993  | Durina |
| 5,234,454 | A |   | 8/1993  | Bangs |
| 5,868,141 | A | * | 2/1999  | Ellias ............................ 128/898 |
| 5,993,473 | A | * | 11/1999 | Chan et al. .................... 606/192 |
| 6,447,027 | B1 |  | 9/2002  | Lilley et al. |
| 6,454,785 | B2 |  | 9/2002  | De Hoyos Garza |
| 6,488,653 | B1 |  | 12/2002 | Lombardo |
| 6,579,301 | B1 |  | 6/2003  | Bales et al. |
| 6,656,194 | B1 |  | 12/2003 | Gannoe et al. |
| 6,675,809 | B2 |  | 1/2004  | Stack |
| 6,994,715 | B2 | * | 2/2006  | Gannoe et al. ............... 606/153 |

(Continued)

FOREIGN PATENT DOCUMENTS

WO   WO 03/055420   * 12/2002

(Continued)

*Primary Examiner* — Corrine M McDermott
*Assistant Examiner* — Mark Mashack
(74) *Attorney, Agent, or Firm* — Patent Law & Venture Group; Gene Scott (57) ABSTRACT

A gastric bariatric balloon includes an upper balloon chamber for sealing against the fundus, a lower balloon chamber for sealing against the antrum and occupying the body of the stomach, and a supplementary chamber for filling at least a portion of the fundus. A tubular inlet is proximal the esophagus entry for receiving a hollow needle. This inlet is filled with a self-sealing material so that when punctured by the needle the material closes the needle hole upon withdrawal of the needle. Spaced apart voids in the material enable fluid interchange between the needle and each of the three chambers separately depending upon the depth of the needle within the inlet tube. Safety arms are mounted on the upper balloon chamber so as to prevent passage of the balloon through the pylorus in case of sudden deflation.

2 Claims, 4 Drawing Sheets

U.S. PATENT DOCUMENTS

| | | |
|---|---|---|
| 2002/0055757 A1 | 5/2002 | Torre et al. |
| 2003/0093117 A1 | 5/2003 | Saadat |
| 2004/0044357 A1* | 3/2004 | Gannoe et al. ................ 606/194 |
| 2004/0199196 A1 | 10/2004 | Ravo |
| 2004/0201216 A1 | 10/2004 | Segal et al. |
| 2005/0192614 A1* | 9/2005 | Binmoeller ................... 606/191 |
| 2005/0267595 A1* | 12/2005 | Chen et al. ................ 623/23.65 |
| 2006/0058735 A1* | 3/2006 | Lesh ......................... 604/93.01 |
| 2007/0078476 A1* | 4/2007 | Hull et al. ..................... 606/191 |
| 2007/0118168 A1* | 5/2007 | Lointier et al. ............... 606/192 |
| 2007/0149994 A1* | 6/2007 | Sosnowski et al. .......... 606/192 |

FOREIGN PATENT DOCUMENTS

| | | |
|---|---|---|
| WO | WO 03/055420 | 7/2003 |

\* cited by examiner

GASTRIC BARIATRIC APPARATUS WITH SELECTIVE INFLATION AND SAFETY FEATURES

BACKGROUND

1. Related Applications
none
2. Field of the Present Disclosure
This disclosure relates generally to an apparatus and method of use of a transesophageal gastric bariatric balloon.
3. Description of Related Art
The following art defines the present state of this field:

Torre et al., U.S 2002/0055757, discloses a space occupying device for deployment within a patient's stomach and methods of deploying and removing the device. The device includes an expandable member and fasteners, such as sutures, that extend to least partially through the patient's stomach wall, and that anchor the device with the patient's stomach. The device can be deployed and/or removed through transesophageal approaches and/or through a combination of transesophageal and transabdominal approaches.

Saadat, U.S. 2003/0093117, discloses an apparatus and methods that are provided for partitioning a gastro-intestinal lumen by intraluminally reducing a local cross-sectional area thereof. The apparatus comprises a plurality of anchors adapted for intraluminal penetration into a wall of the gastro-intestinal lumen to prevent migration or dislodgement of the apparatus, and a partition, which may include a drawstring or a toroidal balloon, coupled to the plurality of anchors to provide a local reduction in the cross-sectional area of the gastro-intestinal lumen.

Ravo, U.S. 2004/0199196, discloses an intraluminal device that has an elongated body member having a series of independent inflatable sections along its length. At least one inflating/deflating line extends from each inflatable section to a distal end of the body member. The device may be used for positing, isolating or identifying a lumen by giving shape to a collapsed viscus. The device may also be used to visualize intraluminal structure or control pressure within a hollow viscus from within the hollow viscus.

Segal et al., U.S. 2004/0201216, discloses a medical connector that is adapted for placement between a catheter and a medical infusion or injection source includes a pair of interlocking half medical connector portions, one side of which attaches to the infusion source and the other side of which is coupled to the catheter connected to the patient and a locking mechanism for locking a medical connector portion to a medical fitting. The connection to the catheter and the infusion source can be via standard medical Luer taper fittings, with or without specially designed locking mechanisms that prevent inadvertent disconnection. The medical connector itself is uniquely shaped and includes a raised surface feature and a recessed surface feature formed on the medical connector portions.

Barnes, U.S. Pat. No. 1,499,962, discloses a pipe joint of the class described, male and female members having axial internally threaded registering bores, the contacting face of the female member having a circular series of spaced arcuate depressions therein defining spaced ribs, and each rib having a portion thereof undercut at corresponding ends communicating with the depression and roughened on the inner face thereof, the contacting face of the male member being provided with a circular series of spaced lugs, an arcuate extension carried by the outer end of each lug projecting in the same direction and in directions opposite to the space ribs, and adapted to be received in the depressions of the female member with the extensions projecting into the undercut portions beneath the ribs and engaging the same with the faces of the male and female members flatly engaging each other, the interlocking connections between the members being confined within the external configuration thereof, and means for preventing relative rotary movement of the members.

Wehrenfennig, U.S. Pat. No. 2,643,581, discloses a bayonet joint for the separable union of an objective with a camera which comprises a camera housing having a light receiving opening with four lugs extending into said opening and spaced to form four notches positioned at the four corners of a rectangular image field and an objective tube having four outwardly projecting lugs positioned to pass through said notches, said tube wall having cut away portions between said lugs to coincide with said notches when said tube is rotated to bring its lugs into engagement with those of said opening, said tube being sealed by a ring-like shoulder beyond said cutaway portions to said housing to prevent leakage of light to the interior of said housing.

Angle, U.S. Pat. No. 3,185,503, discloses a pair of identical annular coupling elements or disks that are constructed and adapted to be connected together to provide a coupling between the adjacent ends of a pair of hose sections, conduits, tubular elements, or the like. The invention is used with various tubular sections forming a garden hose. In such an example the hose sections are usually made form a rubber or plastic material. In addition, it should be understood that the invention may be used with other types of conduits which are made, as an example, from various metals and which are adapted for industrial applications where relatively large fluid pressures are involved such as between a fluid pump and a reservoir.

Dieckmann, U.S. Pat. No. 3,596,936, discloses a quickly connectable attachment system for joining a smaller air tube to a larger cylindrical duct at one end and to an annular terminator device at the other end, including a molded plastic coupling member having coaxial neck and outer cylindrical flange portions with a circular face plate portion therebetween having bayonet slot and protrusion formations thereon, to be fitted on the respective ends of the air tube. A similar integral molding coupling member has a neck to extend through a hole in the side of the larger duct, an outer cylindrical flange to abut the exterior wall of the duct in sealed relation, and a circular flat face plate portion therebetween also having bayonet slots and protrusions to mate with the bayonet protrusions in slots of the first mentioned coupling member. Spring clips slidably and tiltably supported in slots in the second coupling member have shoulder portions extendible through the air passage in the second coupling member to inwardly abut wall portions of the duct and hold the coupling member in place. The terminator device also has a surface to abut the face plate of one of the first coupling members and bayonet protrusions to interfit in bayonet slots of the first coupling member as well as spaces to receive the bayonet protrusions of the first coupling member.

Angelchik, U.S. Pat. No. 4,607,618, discloses a method to treat morbid obesity by implacement in the fundus of a hollow shaped appliance. The appliance is formed of semi-rigid skeleton members and is collapsible to a dimension and shape which can be inserted into the stomach through the esophagus and cardiac opening. Upon release of the collapsed device in the stomach, it autogenously re-assumes its normal uncollapsed shape.

Angelchik, U.S. Pat. No. 4,648,383, discloses an apparatus for peroral treatment of morbid obesity that includes a collapsible intra-gastric appliance which can be temporarily deformed to pass through the esophagus and cardiac opening of the stomach and to autogenously assume a normal shape after it is received in the stomach to stimulate neuro-receptors in the sub-mucosa of the gastric fundus. Means are provided for detachably connecting the appliance to the lower end of an elongate, semi-rigid inserter rod which is passed through an aperture formed in the appliance to effect the detachable connection. Downward pressure on the inserter rod forces the collapsed appliance through the esophagus and cardiac opening into the stomach and slight upward force of the inserter rod is thereafter applied to detach the rod from the appliance.

Weiner et al., U.S. Pat. No. 4,694,827, discloses a balloon that is insertable and inflatable in the stomach to deter ingestion of food and having, when inflated, a plurality of smooth-surfaced convex protrusions disposed to permit engagement of the stomach wall by the balloon only at spaced localities, for minimizing mechanical trauma of the stomach wall by the balloon.

Lai et al., U.S. Pat. No. 4,739,758, discloses a method and apparatus for reducing the size of the stomach cavity in humans. A collapsed balloon is packaged in water-soluble material and releasably attached to a filler tube. The balloon is inserted into the cavity through the mouth and esophagus and pumped up to a desired volume through the tube after water soluble material packaging has dissolved and the balloon deployed. After stomach fluids also dissolve the releasing mechanism, the filler tube is removed from the stomach. The balloon remains in the stomach for the required dieting time. Its volume prevents the usual ingestion of food into the stomach by obese patients, causing them to feel full, and reducing the desire for food. At the end of this period a puncturing mechanism is introduced into the stomach, punctures the balloon, grasps it and the balloon is removed through the esophagus and mouth.

Whitham, U.S. Pat. No. 4,878,695, discloses a joint having no external protrusions that consists of the mating cylindrical nods of two tubular members joined by interlocking cogs on the male and female ends of the tubular members, and a pair of facing ramp surfaced rings disposed in the joint with one ring integral with or affixed immovably to the male end of one tubular member, the other ring rotatably disposed upon that same member within the joint so that when the movable ring is rotated by means of a spanner wrench or equivalent tool relative to the stationary ring, the juxtaposed ramp surfaces ride upon each other causing the movable ring to move axially relative to but in continuing contact with the stationary ring until contact with the female end of the other tubular member in the joint is established and the joint is thereby made rigid. The spaces thus created between the ramps of the rings are filled with material that becomes solid or set screws radially disposed in the movable ring to engage an annular slot about the male end of the one tubular member and underlying the movable ring can be used to thereafter immobilize that ring.

Garren et al., U.S. Pat. No. 4,899,747, discloses a stomach insert for treating obesity in humans by reducing the stomach volume that comprises a flexible, free floating and unattached, inflatable balloon, the balloon being inflatable to a volume effective to reduce the stomach volume of a person being treated. At least a portion of the balloon has a self-sealing substance to facilitate puncture thereof with insufflation means through which the balloon is inflated and to facilitate sealing of the puncture upon removal of the insufflation means. The method herein comprises positioning the balloon inside the stomach of the person being treated for obesity so as to reduce the stomach volume.

Garray et al., U.S. Pat. No. 4,925,446, discloses a removable inflatable beneficial agent delivery device that is adapted to reside in the stomach for a prolonged time period. The device comprises (1) an inflatable member which in its deflated state can be inserted into the stomach via a nasogastric tube and which in its inflated state resides comfortably in the stomach but cannot pass through the pyloric sphincter, (2) an inflation tube connected to the inflatable member by which the inflatable member can be inflated from outside the body and which is dropped into the stomach after inflation, and (3) one or more agent-containing cartridges that are carried exteriorly on the inflatable member or the inflation tube and are capable of delivering agent to the gastrointestinal tract over a prolonged time period.

Gau et al., U.S. Pat. No. 5,084,061, discloses an intragastric balloon that has an ellipsoid or like configuration so that the balloon implanted in the stomach tends to rotate or rock only about one axis when a surgeon attempts to manipulate the balloon, for example, for the purpose of finding a filler valve and inserting a filler tube into it. For easy location, the filler valve is disposed on the equator. A retrieval tab is mounted to the exterior of the balloon, to permit capturing of the balloon and retrieval from the stomach, after the balloon has been deflated and is no longer desired for weight control purposes. Visual and X-ray opaque markers are located in the proximity of the valve and of the retrieval tab to facilitate their visualization with an endoscopic light when the balloon is in the stomach.

Durina, U.S. Pat. No. 5,188,399, discloses a pipe coupling device wherein the connection between pipe members is made by rotating one member relative to the other member so that a plurality of radially extending surfaces of one member face corresponding radially extending surfaces of the other member. The facing surfaces can be flat and planar. The plurality of facing flat surfaces initially face each other in an interlocking arrangement which is not tight. A single threaded adapter is then tightened to draw the plurality of facing surfaces of one member tightly against the corresponding facing surfaces of the other member.

Bangs, U.S. Pat. No. 5,234,454, discloses a method for controlling the body weight of a patient that employs a percutaneous intragastric balloon catheter. The method comprises the first steps of inserting a percutaneous intragastric balloon catheter into the stomach of the patient through a gastrostomy tract. The intragastric balloon catheter, in turn, comprises elongated shaft means having first and second ends, a first inflatable balloon carried proximal to the first end; a second inflatable balloon carried proximal to the first inflatable balloon, the second balloon having a lesser inflated volume than the first balloon; first and second inflation lumens; first and second inflation ports communicating respectively with the first and second inflation lumens and the first and second balloons, which ports are carried by the second end; a drainage lumen passing between said first and second ends. The method continues by inflating the first and second balloons within the patient, partially filling the stomach to provide satiety. The intragastric balloon catheter employed is also deemed to be novel.

Lilley et al., U.S. Pat. No. 6,447,027, discloses a hydrant nozzle for connecting a fire hose to a fire hydrant. The hydrant nozzle comprises a tubular body portion extending longitudinally between a first end and a second end. The body portion has a generally cylindrical outer surface and a generally cylindrical inner surface defining a fluid passageway between the first and second ends. The nozzle further includes a cylindrical neck portion extending from the second end of the body portion to a front face and having an outer peripheral rim and an inner rim defining a center opening in fluid communication with the fluid passageway of the body portion. A pair of spaced apart locking lugs project outwardly from the outer surface and are positioned between the first and second ends of the body portion for removably securing the hydrant nozzle to the fire hydrant. A pair of spaced apart arcuate shaped locking grooves are recessed in the front face of the neck portion between the inner and outer rims for removably securing the hydrant nozzle to the fire hose.

De Hoyos Garza, U.S. Pat. No. 6,454,785, discloses an invention that relates to a percutaneous intragastric balloon catheter for the treatment of obesity. The invention occupies a portion of the gastric cavity causing a feeling of satiety and decreasing the consumption of food by an obese patient. This invention consists in a percutaneous intragastric balloon that is placed in a non-surgically form. The percutaneous intragastric balloon catheter is collocated by percutaneous endoscopic gastronomy (PEG). The invention comprises an affixed valve for regulating the amount of fluid introduced or evacuated from the percutaneous intragastric balloon.

Lombardo, U.S. Pat. No. 6,488,653, discloses a dilation balloon catheter comprising a non-compliant balloon attached to a catheter, the balloon portion includes a plurality of sections having different outer diameters, as measured at the central portion or midpoint of the section, when the balloon is inflated. In one embodiment that is deployable from an endoscope to treat esophageal, pyloric, or colonic strictures, a series of progressively larger balloon sections are used to safely dilate the stricture in stages. Each section includes a central portion having a waist for centering the balloon over the stricture, with the distal section having the smallest diameter and the intermediate and proximal sections being about 2 and 4 mm larger, respectively. A wire guide extends throughout the length of the catheter and balloon and forms a distal portion of the dilation balloon catheter for assisting in cannulation of the stricture. Optionally, the dilation balloon catheter can include a series of bands or other markings to indicate the location of the different balloon sections. These indicia can be located on the wire guide or the balloon material and may be radiopaque.

Bales et al., U.S. Pat. No. 6,579,301, discloses an intragastric balloon device that includes a flexible bladder, a relatively rigid reservoir coupled to the bladder and adapted to hold a bladder inflation fluid, and an inflation/deflation system adapted to move or permit movement of the fluid from the reservoir and into the bladder. The intragastric balloon device is sized such that it may be positioned, in its entirety, into the stomach cavity. Various systems may be used to move or permit movement of the fluid. A control system is provided to automatically activate the inflation/deflation system. The automatic activation may be activated by a combination of one or more of a timer, the temperature of the stomach, the pressure in the stomach, the mechanical stress in the stomach, or another sensed condition, at which the control system is programmed or otherwise configured to activate.

Gannoe et al., U.S. Pat. No. 6,656,194, discloses magnetic anchoring devices that are disclosed herein. Expandable devices that are inserted into the stomach of a patient are attached to its interior wall by magnetically coupling. Such expandable devices, like inflatable balloons, comprise at least one magnetic device, which may be a magnet, a magnetizable material, or a magnetic metal. The magnetic device may be positioned on the external or interior surface of the expandable device or may be integral thereto. The magnetic device is magnetically coupled to a magnetic anchor positioned on a surface of the stomach wall. In this way, the expandable devices are anchored to the stomach walls, preventing migration of the device to other areas of the body where they may become obstructions and pose health risks.

Stack et al., U.S. Pat. No. 6,675,809, discloses a device for inducing weight loss in a patient that includes a tubular prosthesis that is self-expandable from a collapsed position in which the prosthesis has a first diameter to an expanded position in which the prosthesis has a second, larger, diameter. In a method for inducing weight loss, the prosthesis is placed in the collapsed position and inserted into a stomach of a patient. The prosthesis is allowed to self-expand from the collapsed position to the expanded position and into contact with the walls of the stomach, where it induces feelings of satiety and/or inhibits modulation of satiety-controlling factors such as Ghrelin.

Lointier, WO 03/055420, discloses an invention that concerns an expansible introgastric balloon for treating obesity, designed to be implanted in the stomach to reduce its volume, said balloon comprising a first flexible pouch provided with first connecting means, for receiving a connecting member designed to be connected to a first fluid source, to expand said first pouch in the stomach by filling it with the fluid. The invention is characterized in that it comprises at least a second flexible pouch provided with second connecting means, said second connecting means being separated from the first connecting means, so as to be connected to a second fluid source different from the first fluid sources. The invention is useful for treating obesity.

Our prior art search with abstracts described above teaches the construction, placement, use and removal of gastric balloons. The present disclosure distinguishes over the prior art by teaching a gastric balloon with an inlet valve system enabling gaseous fluid exchange between an injection needle and any one of three separate balloon chambers. The present invention further distinguishes over the prior art by teaching the use of safety arms for preventing the balloon from being swallowed through the pylorus valve.

SUMMARY

This disclosure teaches certain benefits in construction and use which give rise to the objectives described below.

A gastric bariatric balloon includes an upper balloon chamber for sealing against the fundus, a lower balloon chamber for sealing against the antrum, a central portion for sealing against the body of the stomach, and one or more supplementary chambers for further filling portions of the fundus. A tubular inlet is positioned proximal to the esophageal entry for receiving a hollow needle therein. This inlet is filled with a self-sealing material so that when punctured by the needle the material closes the needle hole upon withdrawal of the needle. Spaced apart voids in the material enable fluid interchange between the needle and each of the three independent chambers depending upon the depth of the needle within the inlet tube. Safety arms are mounted on the upper balloon chamber so as to prevent passage of the balloon through the pylorus in case of sudden deflation.

A primary objective inherent in the above described apparatus and method of use is to provide advantages not taught by the prior art.

Another objective is to enable the inflation and deflation of plural independent balloon chambers.

A further objective is to prevent the balloon from passing through the pylorus in case of sudden deflation.

A still further objective is to adjust the stomach volume occupied by the balloon without removing the balloon from the stomach.

Other features and advantages of the described apparatus and method of use will become apparent from the following more detailed description, taken in conjunction with the accompanying drawings, which illustrate, by way of example, the principles of the presently described apparatus and method of its use.

BRIEF DESCRIPTION OF THE DRAWINGS

The accompanying drawings illustrate at least one of the best mode embodiments of the present apparatus and method of it use. In such drawings.

DETAILED DESCRIPTION

The above described drawing figures illustrate the described apparatus and its method of use in at least one of its preferred, best mode embodiment, which is further defined in detail in the following description. Those having ordinary skill in the art may be able to make alterations and modifications what is described herein without departing from its spirit and scope. Therefore, it must be understood that what is illustrated is set forth only for the purposes of example and that it should not be taken as a limitation in the scope of the present apparatus and method of use.

The presently described gastric bariatric apparatus is designed for placement within a patient's stomach 10 in order to reduce the stomach's volume so as to control the patient's weight and provide ongoing weight loss. The apparatus may be used for reducing stomach volume in applications where surgical volume reduction has already been accomplished. The human stomach 10 has an interior surface 12 defining a stomach volume. This volume includes a fundus 16, an antrum 18 and a body 17 portions as defined and shown in FIG. 1.

Figures 1, 2:
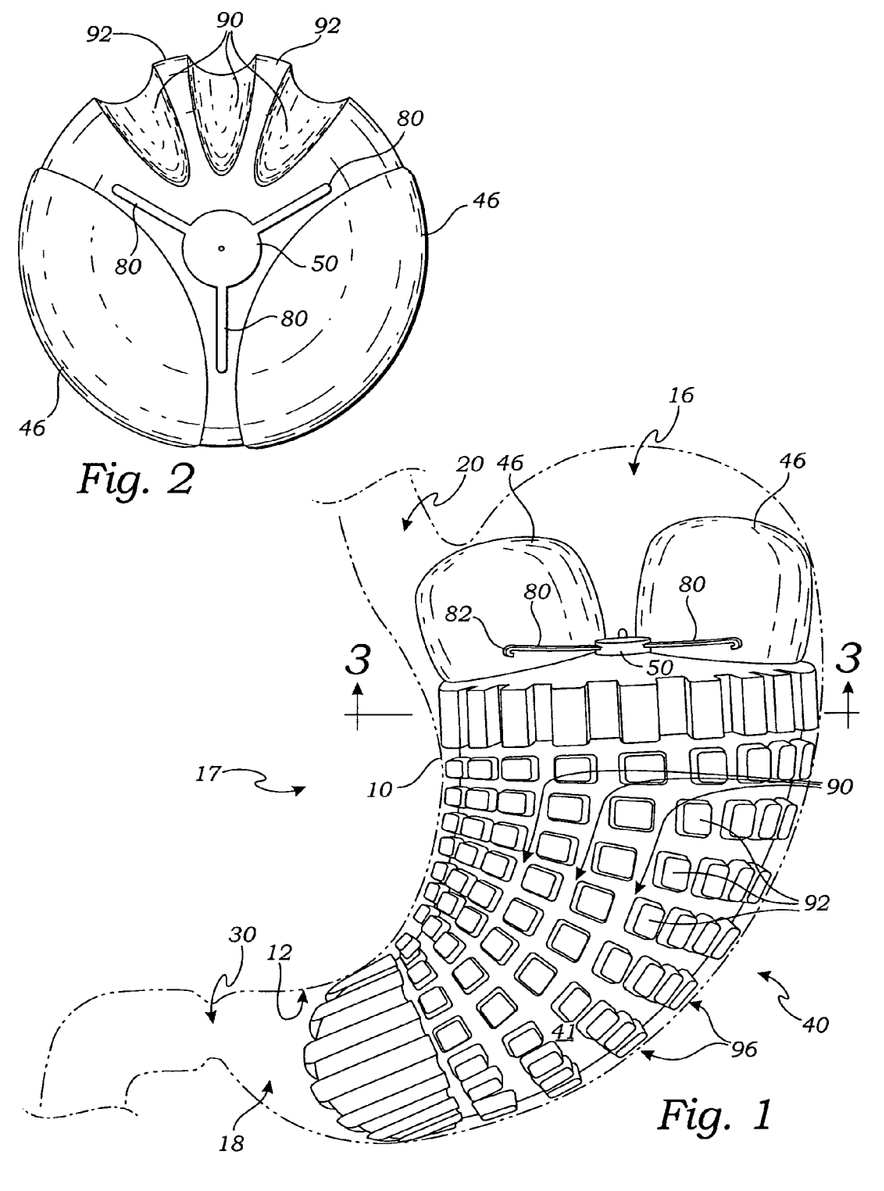
FIG. 1 is a side elevational view of the instant apparatus as fully inflated and seated within the stomach.
FIG. 2 is a top plan view thereof.

The esophagus entry 20 and a pylorus discharge valve 30 define the entry and exit points respectively for foods as they are digested and pass through the stomach 10. The instant apparatus is a collapsible gastric balloon 40 having an upper balloon chamber 42 for sealing against the fundus 16, a lower balloon chamber 44 for sealing against the body 17 as well as the antrum 18 and one or more supplementary balloon chamber 46 which may be used for filling at least a portion of the fundus 16. The term "supplementary balloon chamber 46" as defined herein means one, two, three, or more separate chambers, all in fluid communication with each other, as is clearly shown in FIG. 3. By adjusting the size of the supplementary chamber 46 through air inflation, the total volume of the balloon 40 may be changed quickly and easily to adjust the amount of the stomach's volume that is available for digestion, and this can be done with the balloon 40 in place as will be described below. Also, the upper balloon chamber 42 may be inflated to a more or lesser extent for the same purpose, and again, without removing the balloon 40 from the stomach 10.

Figure 3:
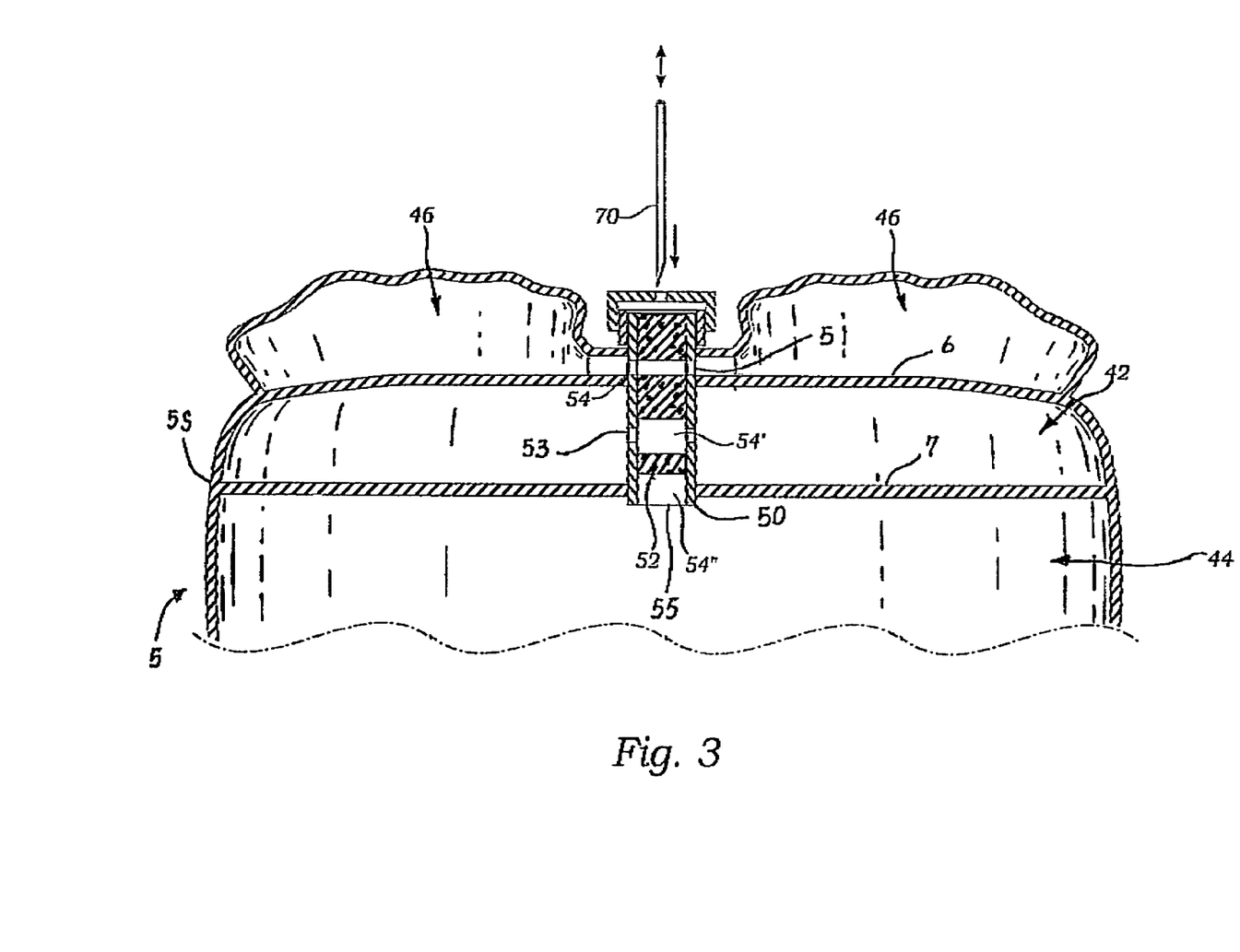
FIG. 3 is a vertical sectional view showing an upper balloon chamber, a lower balloon chamber and supplemental balloon chambers and their interconnection with a tubular inlet valve.
Figures 4, 5, 6, 7:
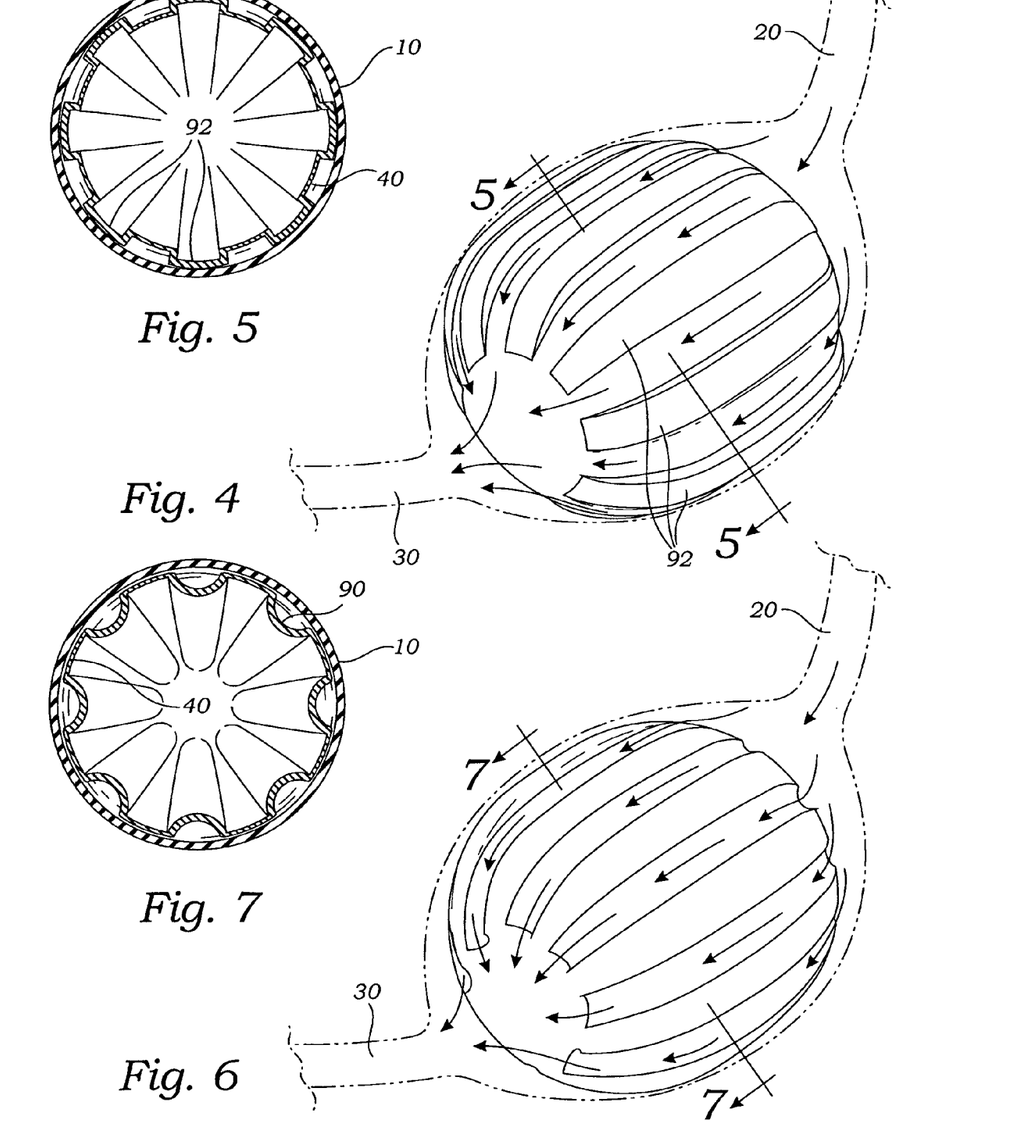
FIG. 4 is a perspective view of an embodiment showing longitudinal ridges on the exterior of the gastric balloon.
FIG. 5 is a sectional view thereof taken along line 5-5 in FIG. 4.
FIG. 6 is a perspective view of an embodiment showing longitudinal channels on the exterior of the gastric balloon.
FIG. 7 is a sectional view thereof taken along line 7-7 in FIG. 6.
Figures 8, 9:
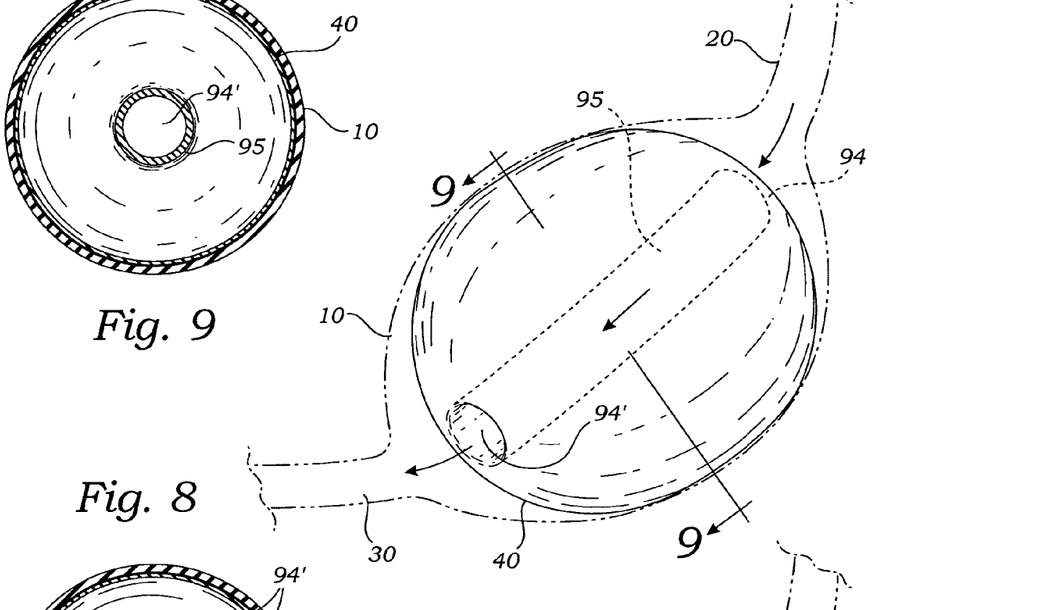
FIG. 8 is a perspective view of an embodiment showing a longitudinal passage within the gastric balloon.
FIG. 9 is a sectional view thereof taken along line 9-9 in FIG. 8.
Figures 10, 11:
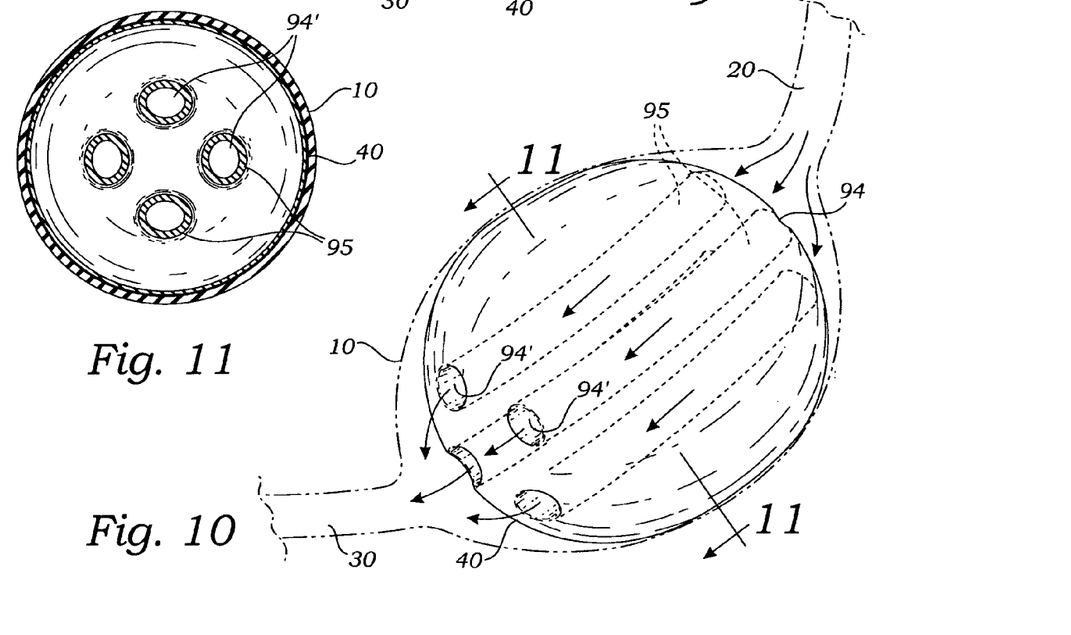
FIG. 10 is a perspective view of an embodiment showing plural longitudinal passages within the gastric balloon.
FIG. 11 is a sectional view thereof taken along line 11-11 in FIG. 10.

A tubular inlet 50 is mounted in the upper balloon chamber 42 and positioned proximal to the esophagus entry 20 so that it may be entered by an esophageal probe, e.g., a modified gastroscope. This inlet tube 50 is filled with a self-sealing material 52 of a type that is well known in medical arts. Such materials 52 will accept an injection needle or other hollow needle and upon removal, the puncture quickly seals itself. Within the material 52 an upper medial void 54 is integral with the supplementary chamber 46. A lower medial void 54' within the self-sealing material 52 is integral with the upper balloon chamber 42. Finally, a distal void 54" within the self-sealing material 52 is integral with the lower balloon chamber 44. An injection needle 70 may therefore be inserted into the tubular inlet 50 terminating within the upper medial void 54 for gaseous fluid interchange with the supplementary chamber 46, within the lower medial void 54' for gaseous fluid interchange with the upper balloon chamber 42, and within the distal void 54" for gaseous fluid interchange with the lower balloon chamber 44. Therefore, any one of these three chambers may be inflated or deflated without affecting the other two. When such fluid interchange is completed, the needle 70 may withdrawn without appreciable further fluid flow through the puncture created by the needle within the material 52. Typically, the inflation fluid is air.

The apparatus further preferably comprises plural safety arms 80 proximally engaged with the upper balloon chamber 42 as shown in FIG. 1. The safety arms 80 are of such extension and rigidity, although somewhat flexible, as to prevent the apparatus from being passed through the pylorus discharge valve 30 in the event of deflation of the upper 42, lower 44 and supplemental 46 balloon chambers. Arms 80, however, can be flexed into a longitudinal position so as to be passed through the esophagus for placing the apparatus into the stomach. 10.

Preferably, terminal ends 82 of each of the safety arms 80 are curled backwardly, as shown in FIG. 1. This provides a curved surface for contact with the stomach's interior tissues which helps to prevent tearing upon contact.

The upper balloon chamber 42 is expansive for sealing against the surfaces of the fundus 16 providing a mechanical gripping and holding action so that the balloon 40 remains in place at the desired location within the stomach 10. The lower balloon chamber 44 is also expansive for contacting the stomach interior surface 12 for sealing against the antrum 18 so that the balloon 40 remains in its desired location within the stomach. 10. The supplemental chamber(s) 46 is/are expansive for filling the fundus to the extent desired and are typically used as a supplemental expedient to the upper balloon chamber 42.

The gastric balloon 40 provides a means for passing digested materials from the esophagus entry 20 to the pylorus discharge valve 30 when the gastric balloon 40 is fully inflated and sealed against the interior of the stomach 10. This passage may comprise one or more alternative enablements including: a plurality of longitudinally oriented channels 90 or ridges 92 in an exterior surface 41 of the gastric balloon 40, or one or more conduits 95 having an entry 94 on a surface of the upper balloon 42, and an exit 94' on a surface of the lower balloon 44.

In a yet further embodiment, the gastric balloon preferably provides a plurality of interconnecting circumferential ridges 96 on its outer surface for reducing contact between the apparatus and the stomach interior surface 12.

Returning to FIG. 3 now, we see that the gastric bariatric balloon has an outer skin 5 fully enclosing the three chambers now referred to as the first 46, second 42 and third 44 chambers within the gastric bariatric balloon 40, the outer skin 5 having an exterior surface 5S. The first 46 and second 42 said chambers are separated by a first partition 6 while the second 42 and third 44 said chambers separated by a second partition 7. The linear tubular inlet 50 penetrates the outer skin 5 and the first 6 and second 7 partitions. The tubular inlet 50 has a first aperture 51 located for enabling fluid communication between the tubular inlet 50 and the first chamber 46, and a second aperture 53 enabling fluid communication between the tubular inlet 50 and the second chamber 42, and a third aperture 55 enabling fluid communication between the tubular inlet 50 and the third chamber 44. The self-sealing material 52 is located within the tubular inlet 50 in three locations; in a first location preventing fluid communication between the exterior surface 5S and the first aperture 51, in a second location preventing fluid communication between the first 51 and second 53 apertures, and in a third location preventing fluid communication between the second 53 and third 55 apertures as shown in FIG. 3. Therefore, insertion of the fine tube or needle 70 into the tubular inlet 50 is able to exchange fluid with the first 46, second 42 or third 44 chambers through the first 51, second 53 or third 55 apertures respectively depending on the inserted position of the fine needle 70.

The enablements described in detail above are considered novel over the prior art of record and are considered critical to the operation of at least one aspect of the apparatus and its method of use and to the achievement of the above described objectives. The words used in this specification to describe the instant embodiments are to be understood not only in the sense of their commonly defined meanings, but to include by special definition in this specification: structure, material or acts beyond the scope of the commonly defined meanings. Thus if an element can be understood in the context of this specification as including more than one meaning, then its use must be understood as being generic to all possible meanings supported by the specification and by the word or words describing the element.

The definitions of the words or drawing elements described herein are meant to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements described and its various embodiments or that a single element may be substituted for two or more elements in a claim.

Changes from the claimed subject matter as viewed by a person with ordinary skill in the art, now known or later devised, are expressly contemplated as being equivalents within the scope intended and its various embodiments. Therefore, obvious substitutions now or later known to one with ordinary skill in the art are defined to be within the scope of the defined elements. This disclosure is thus meant to be understood to include what is specifically illustrated and described above, what is conceptually equivalent, what can be obviously substituted, and also what incorporates the essential ideas.

The scope of this description is to be interpreted only in conjunction with the appended claims and it is made clear, here, that each named inventor believes that the claimed subject matter is what is intended to be patented.

What is claimed is:

1. An inflatable gastric bariatric apparatus capable of being inserted into a stomach, and thereafter expanded, the apparatus comprising:
   a tubular inlet extending into communication with chambers of the apparatus;
   three safety arms engaged with the tubular inlet immediately adjacent and exterior to an upper balloon chamber of the apparatus, the safety arms extending laterally and radially from the tubular inlet; and
   at least two supplemental balloon chambers secured in opposing positions around the tubular inlet and safety arms, and exterior to the upper balloon chamber, the supplemental balloon chambers, when inflated, are positioned to prevent contact between the plural safety arms and an interior surface of the stomach.

2. The apparatus of claim 1 further comprising a plurality of circumferential ridges on an outer surface of the apparatus, said ridges defining parallel channels.

\* \* \* \* \*